United States Patent
Linford et al.

(10) Patent No.: US 9,217,734 B2
(45) Date of Patent: *Dec. 22, 2015

(54) THIN LAYER CHROMATOGRAPHY PLATES AND RELATED METHODS

(75) Inventors: Matthew R. Linford, Orem, UT (US); Robert C. Davis, Provo, UT (US); Richard Vanfleet, Provo, UT (US); David Scott Jensen, Provo, UT (US); Li Yang, Sunnyvale, CA (US); Jun Song, Clifton Park, NY (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 352 days.

This patent is subject to a terminal disclaimer.

(21) Appl. No.: 12/826,940

(22) Filed: Jun. 30, 2010

(65) Prior Publication Data

US 2011/0000852 A1    Jan. 6, 2011

Related U.S. Application Data

(60) Provisional application No. 61/270,023, filed on Jul. 1, 2009.

(51) Int. Cl.
| | |
|---|---|
| *G01N 30/92* | (2006.01) |
| *B01J 20/20* | (2006.01) |
| *B01J 20/28* | (2006.01) |
| *B01J 20/282* | (2006.01) |
| *B01J 20/286* | (2006.01) |
| *B82Y 30/00* | (2011.01) |

(52) U.S. Cl.
CPC .............. *G01N 30/92* (2013.01); *B01J 20/205* (2013.01); *B01J 20/282* (2013.01); *B01J 20/286* (2013.01); *B01J 20/28007* (2013.01); *B82Y 30/00* (2013.01); *B01J 2220/54* (2013.01)

(58) Field of Classification Search
CPC .. B01J 20/205; B01J 20/28007; B01J 20/282; B01J 20/286; B01J 2220/54; G01N 30/92; B82Y 30/00
USPC ................. 210/658, 198.3; 73/61.54; 422/70; 436/162
See application file for complete search history.

(56) References Cited

U.S. PATENT DOCUMENTS

| | | | |
|---|---|---|---|
| 4,276,061 A * | 6/1981 | Nestrick et al. ................... | 95/88 |
| 6,749,814 B1 | 6/2004 | Bergh et al. | |

(Continued)

FOREIGN PATENT DOCUMENTS

| | | |
|---|---|---|
| CN | 1970128 | 5/2007 |
| CN | 102472733 | 5/2012 |

(Continued)

OTHER PUBLICATIONS

U.S. Appl. No. 13/035,645, Oct. 24, 2012, Notice of Allowance.

(Continued)

*Primary Examiner* — Ernest G Therkorn
(74) *Attorney, Agent, or Firm* — Dorsey & Whitney LLP (57) ABSTRACT

In an embodiment, a method for manufacturing a thin layer chromatography ("TLC") plate is disclosed. The method includes forming a layer of elongated nanostructures (e.g., carbon nanotubes), and at least partially coating the elongated nanostructures with a coating. The coating includes a stationary phase and/or precursor of a stationary phase for use in chromatography. Embodiments for TLC plates and related methods are also disclosed.

18 Claims, 7 Drawing Sheets

(56) References Cited

U.S. PATENT DOCUMENTS

| | | | |
|---|---|---|---|
| 6,858,434 B1 | 2/2005 | Williams | |
| 7,413,723 B2 * | 8/2008 | Niu et al. | 423/447.3 |
| 8,038,887 B2 * | 10/2011 | Bakajin et al. | 210/652 |
| 2005/0176245 A1 | 8/2005 | Melechko et al. | |
| 2006/0159916 A1 | 7/2006 | Dubrow et al. | |
| 2007/0193934 A1 | 8/2007 | Shukla et al. | |
| 2007/0237681 A1 | 10/2007 | Boyle et al. | |
| 2008/0223795 A1 * | 9/2008 | Bakajin et al. | 210/767 |
| 2009/0085426 A1 | 4/2009 | Davis et al. | |
| 2009/0086923 A1 | 4/2009 | Davis et al. | |
| 2009/0320991 A1 * | 12/2009 | Boyle et al. | 156/151 |

FOREIGN PATENT DOCUMENTS

| | | |
|---|---|---|
| WO | WO 2004/059298 | 7/2004 |
| WO | WO 2008/048247 | 4/2008 |
| WO | WO 2008/097360 | 8/2008 |
| WO | WO 2011/002844 | 1/2011 |
| WO | WO 2011/106694 | 9/2011 |

OTHER PUBLICATIONS

International Search Report and Written Opinion from International Appliction No. PCT/US2011/026313 dated May 30, 2011.
Brinkman et al: "Stationary phases for high-performance thin-layer chromatography" Journal of Chromatography, vol. 198, No. 4, 1980—pp. 421-428.
Brinkman et al: "Thin-layer chromatography on chemically bonded phases: a comparison of pre-coated plates", Journal of Chromatography, vol. 258, 1983—pp. 43-55.
Luong et al: "Electrophoretic separation of aniline deriviatives using fused silica capillaries coated with acid treated single-walled carbon nanotubes", Journal of Chromatography, vol. 1074, No. 1-2, 2005—pp. 187-194.
Shubhodeep Goswami et al: "Aligned Carbon Nanotube Stationary Phases for Electochromatographic Chip Separations" Chromatographia; An International Journal for Rapid Communication in Chromatography, Electophoresis and Associated Techniques, Vieweg Verlag, WI, vol. 69, No. 5-6, Feb. 3, 2009, pp. 473-480.
Fonverne et al: "In situ Synthesized Carbon Nanotubes as a New Nanostructured Stationary Phase for Microfabricated Liquid Chromatographic Column", Sensors and Actuators B, Elsevier Sequoia S.A., Lausanne, CH LNKD-DOI: 10.1016/J.SNB.2007.08.049, vol. 129, No. 2, Feb. 13, 2008, pp. 510-517.
International Search Report and Written Opinion mailed Sep. 3, 2010 for PCT/US/2010/040532.
Zhang et al: "Analysis of channel-geometry effects on separation efficiency in rectangular-capillary electrochromatography columns" Journal of Chromatography A, 869 (2000) 319-328.
Pra et al: "Experimental Study on Band Dispersion in Channels Structured with Micropillars" Anal. Chem, 2006, 78, 6519-6525.
Yamada et al: "Size-selective growth of double-walled carbon nanotube forests from engineered iron catalysts" nature nanotechnology, vol. I, Nov. 2006, 131-136.
Malsche et al: "Experimental Study of Porous Silicon Shell Pillars under Retentive Conditions" Anal. Chem. 2008, 80, 5391-5400.
Smet et al: "Influence of the Pillar Shape on the Band Broadening and the Separation Impedance of Perfectly Ordered 2-D Porous Chromatographic Media" Anal. Chem, 2004, 76, 3716-3726.
Gzil et al: "Advantages of Perfectly Ordered 2-D Porous Pillar Arrays over Packed Bed Columns for LC Separations: A Theoretical Analysis" Anal. Chem, 2003, 75, 6244-6250.
Gzil et al: "General Rules for the Optimal External Porosity of LC Supports" Anal Chem, 2004, 76, 6707-6718.
U.S. Appl. No. 12/958,595, Sep. 11, 2012, Office Action.
U.S. Appl. No. 13/035,645, Sep. 11, 2012, Office Action.
U.S. Appl. No. 12/958,595, Dec. 10, 2012, Notice of Allowance.
U.S. Appl. No. 61/339,095, filed Feb. 26, 2010, Linford et al.
U.S. Appl. No. 61/945,628, filed Feb. 27, 2014, Linford et al.
Sun ; "Study on Growth and Mechanism of Single-Walled Carbon Nanotubes on Silicon Substrate", Wanfang Database of Dissertations, dated Jan. 16, 2007; published on Mar. 17, 2008, pp. 1-51; English Absract located on p. 3.
Fang et al.: "Preparation and CO conversion activity of ceria nanotubes by carbon nanotubes templating method", Journal of Rare Earths, vol. 26, No. 2, Apr. 2008, p. 153-157.
Zhang et al.: "Carbon nanotube-assisted synthesis and high catalytic activity of CeO2 hollow nanobeads", Materials Chemistry and Physics, vol. 113 (2009) 527-530.
Zhou, et al.: "Progress in preparation and Applications of Aligned Carbon Nanotubes Arrays", Center for Photon Manufacturing Science, pp. 95-98, May 21, 2007.
Zhun, et al.; "Progress in research on growth mechanism of carbon nanotubes",China Symposium on Active Carbon in 2008; Research Institute of Chemical Defense, Beijing 100083; pp. 181-184; Nov. 1, 2008.
U.S. Appl. No. 12/958,595, May 26, 2015, Notice of Allowance.
U.S. Appl. No. 13/035,645, Mar. 25, 2015, Notice of Allowance.
U.S. Appl. No. 12/958,595, Oct. 2, 2015, Issue Notification.
U.S. Appl. No. 13/035,645, Oct. 29, 2015, Notice of Allowance.
U.S. Appl. No. 60/995,881, filed Sep. 28, 2007, Davis et al.
U.S. Appl. No. 12/239,281, filed Sep. 26, 2008, Davis et al.
U.S. Appl. No. 61/270,023, filed Jul. 1, 2009, Linford et al.
U.S. Appl. No. 61/283,281, filed Dec. 2, 2009, Linfold et al.
U.S. Appl. No. 12/958,595, filed Dec. 2, 2010, Linfold et al.
U.S. Appl. No. 13/035,645, filed Feb. 25, 2011, Linfold et al.

* cited by examiner

THIN LAYER CHROMATOGRAPHY PLATES AND RELATED METHODS

CROSS-REFERENCE TO RELATED APPLICATIONS

This application claims the benefit of U.S. Provisional Application No. 61/270,023 filed on 1 Jul. 2009, entitled "Binder Free Think Layer Chromatography Plates Assembled Through Carbon Nanotubes," which is hereby incorporated herein, in its entirety, by this reference.

BACKGROUND

Chromatography and solid-phase extraction ("SPE") are commonly-used separation techniques employed in a variety of analytical chemistry and biochemistry environments. Chromatography and SPE are often used for separation, extraction, and analysis of various constituents, or fractions, of a sample of interest. Chromatography and SPE may also be used for the preparation, purification, concentration, and clean-up of samples.

Chromatography and SPE relate to any of a variety of techniques used to separate complex mixtures based on differential affinities of components of a sample carried by a mobile phase with which the sample flows, and a stationary phase through which the sample passes. Typically, chromatography and SPE involve the use of a stationary phase that includes an adsorbent packed into a cartridge, column, or disposed as a thin layer on a plate. Thin-layer chromatography ("TLC") employs a stationary phase that is spread in a thin layer on a carrier or substrate plate. A commonly-used stationary phase includes a silica-gel-based sorbent material.

Mobile phases are often solvent-based liquids, although gas chromatography typically employs a gaseous mobile phase. Liquid mobile phases may vary significantly in their compositions depending on various characteristics of the sample being analyzed and on the various components sought to be extracted and/or analyzed in the sample. For example, liquid mobile phases may vary significantly in pH and solvent properties. Additionally, liquid mobile phases may vary in their compositions depending on the characteristics of the stationary phase that is being employed. Often, several different mobile phases are employed during a given chromatography or SPE procedure.

A typical TLC plate is prepared by mixing an adsorbent (which acts as the stationary phase) with a small amount of an inert binder and water. The mixture may be spread as a relatively viscous slurry onto a carrier sheet. The resulting plate can then be dried and activated in an oven. The resulting stationary phase is bound in place to the carrier sheet or other substrate by the binder. The presence of the binder can lead to secondary interactions with the mobile phase, as well as a decrease in separation efficiency.

SUMMARY

Embodiments of the present invention are directed to TLC plates, methods of using such TLC plates in chromatography, and related methods of manufacture in which a plurality of porous elongated stationary phase structures are formed and affixed to a substrate without the use of a separate binder. The elimination of the use of any binder may prevent unwanted secondary interactions, as well as may improve separation efficiency.

In an embodiment, a method for manufacturing a TLC plate is disclosed. The method includes forming a layer of elongated nanostructures, and at least partially coating the elongated nanostructures with a coating. The coating includes a stationary phase and/or a precursor of a stationary phase for use in chromatography. In an embodiment, the elongated nanostructures may subsequently be removed by heating in an oxidizing environment so as to burn off the elongated nanostructures.

In an embodiment, a TLC plate is disclosed. The TLC plate includes a substrate, and a plurality of porous stationary phase structures that extend longitudinally away from the substrate. At least a portion of the plurality of porous stationary phase structures exhibits an elongated annular geometry.

In an embodiment, a method of performing chromatography is disclosed. The method includes providing a TLC plate including a substrate, and a plurality of porous stationary phase structures extending longitudinally away from the substrate. At least a portion of the plurality of porous stationary phase structures exhibits an elongated annular geometry. The method further includes applying a sample to be analyzed to the plurality of porous stationary phase structures of the TLC plate, and drawing a mobile phase through the plurality of stationary phase structures having the sample applied thereto. The different components of the sample may be separated as the mobile phase and the sample interact with the TLC plate.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

FIG. 10CC is a close-up top plan view of one of the coated CNTs of FIG. 10C.

FIG. 10DD is a close-up top plan view similar to FIG. 10CC, but once the CNTs have been burned off;

DETAILED DESCRIPTION

I. Introduction

Embodiments of the present invention are directed to TLC plates and related methods of manufacture and use. The disclosed TLC plates may include a plurality of porous elongated stationary phase structures affixed to a substrate without the use of a separate binder to provide a highly porous structure suitable for chromatography applications. The elimination of the use of any binder may prevent unwanted secondary interactions, as well as may improve separation efficiency.

II. Embodiments of Methods for Manufacturing TLC Plates and TLC Plate Embodiments In various embodiments, a TLC plate may be manufactured by forming a layer of elongated nanostructures on a substrate and then at least partially coating the elongated nanostructures with a coating that comprises a stationary phase and/or a precursor to the stationary phase for use in chromatography. While the description hereinbelow uses carbon nanotubes ("CNTs) as an example of a suitable elongated nanostructure, other elongated nanostructures may be used, such as semiconductor nanowires with or without a porous coating, metallic nanowires with or without a porous coating, nanopillars formed by nanoimprint lithography, combinations of the foregoing, or any other suitable nanostructure.

The substrate may include a base, a backing layer disposed on the base, and a catalyst layer disposed on the backing layer that is used to catalyze growth of CNTs over the substrate. Generally, the catalyst layer may be deposited onto the backing layer by any suitable technique. For example, placement of the catalyst layer may be accomplished using a photolithography process, such as masking the catalyst layer and etching to remove regions of the catalyst layer exposed through the mask. Such photolithography processes may be used to produce a catalyst layer having a selected pattern. In another embodiment, the catalyst layer may be applied so as to coat substantially the entire substrate.

The catalyst layer may comprise any suitable material that catalyzes growth of CNTs under suitable growing conditions (e.g., heating and exposure to a process gas such as $H_2$ and a carbon containing gas such as $C_2H_4$). Various transition metals may be suitable for use as a catalyst layer. Suitable metals include, but are not limited to iron, nickel, cobalt, alloys of the forgoing metals, and combinations thereof.

The backing layer of the substrate provides support for the structures of the TLC plate. For example, the backing layer provides a support on which the catalyst layer may be deposited, and may also function as a diffusion barrier to help prevent a chemical reaction between the catalyst layer and the base. Examples of backing layer materials may include, but are not limited to, silica, alumina, a low-expansion high-temperature borosilicate glass (e.g., Pyrex 7740 and/or Schott Borofloat glass), steel (e.g., stainless steel), a silicon wafer, or any other high-temperature glass or other suitable material. In embodiments where the backing layer comprises a material other than alumina, the backing layer may be prepared for CNT growth by application of a thin layer of alumina over the backing layer. The alumina layer may have a thickness between about 5 nm and about 100 nm, more specifically between about 10 nm and about 50 nm, and most specifically between about 20 nm and about 40 nm.

Figure 1:
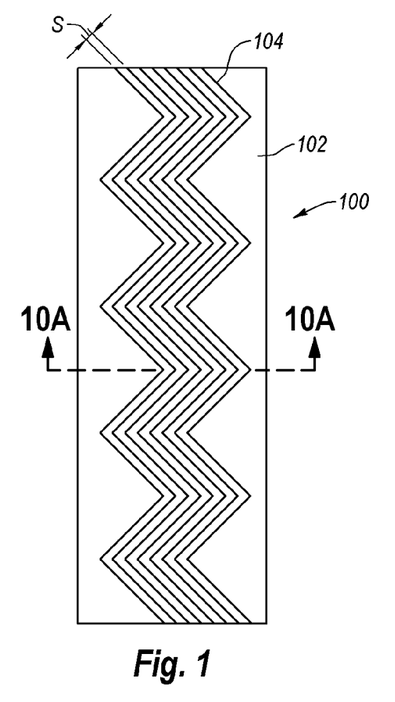
FIG. 1 is a schematic top plan view of an embodiment of a TLC plate intermediate structure including a substrate and a catalyst layer disposed over the substrate, with the catalyst layer exhibiting a zigzag pattern.
Figure 2:
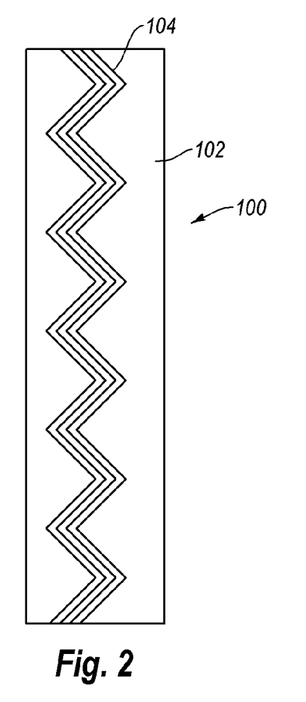
FIG. 2 is a schematic top plan view of another embodiment of a TLC plate intermediate structure similar to FIG. 1, but the catalyst layer exhibits an alternative zigzag pattern.
Figure 3:
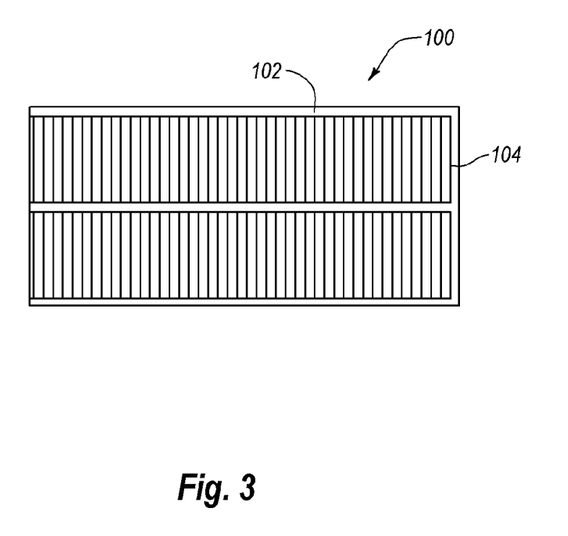
FIG. 3 is a schematic top plan view of another embodiment of a TLC plate intermediate structure similar to FIG. 1, but the catalyst layer exhibits a substantially parallel spacing pattern.
Figure 4:
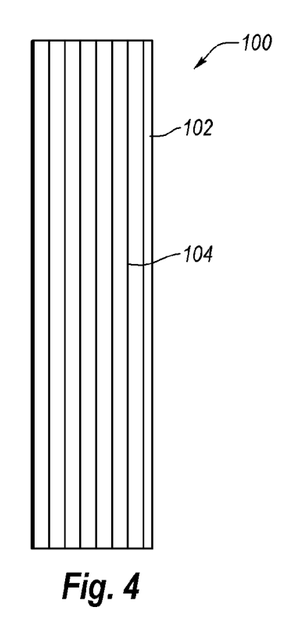
FIG. 4 is a schematic top plan view of another embodiment of a TLC plate intermediate structure similar to FIG. 3, but the catalyst layer exhibits another substantially parallel spacing pattern.
Figure 5:
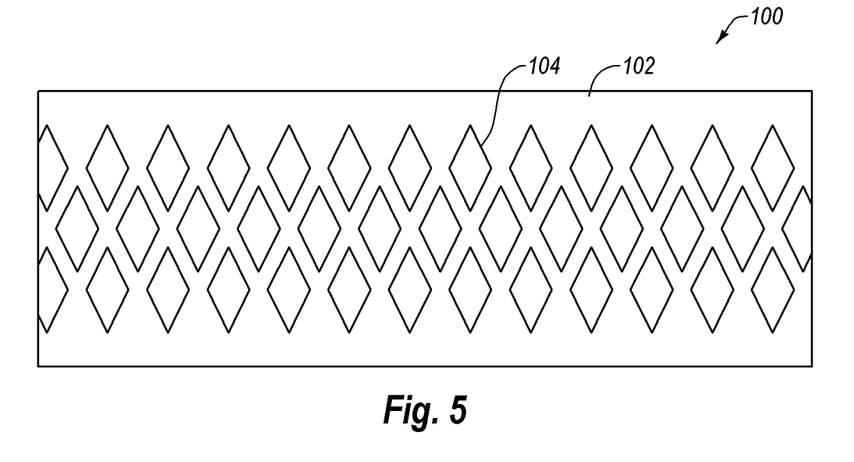
FIG. 5 is a schematic top plan view of another embodiment of a TLC plate intermediate structure similar to FIG. 1, but the catalyst layer exhibits a diamond-shaped pattern.
Figure 6:
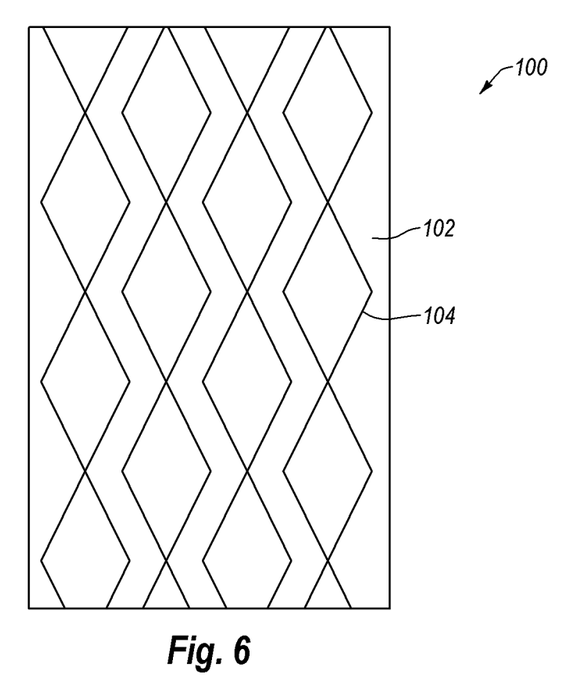
FIG. 6 is a schematic top plan view of another embodiment of a TLC plate intermediate structure similar to FIG. 5, but the catalyst layer exhibits another diamond-shaped pattern.
Figure 7:
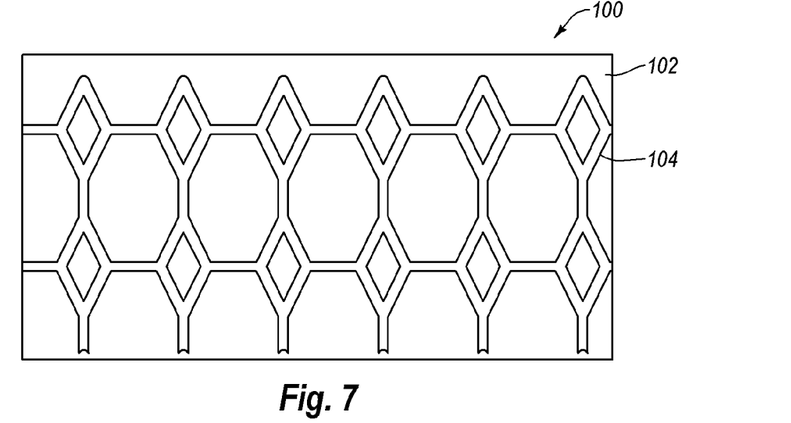
FIG. 7 is a schematic top plan view of another embodiment of a TLC plate intermediate structure similar to FIG. 1, but the catalyst layer exhibits a honeycomb-like pattern.
Figure 8:
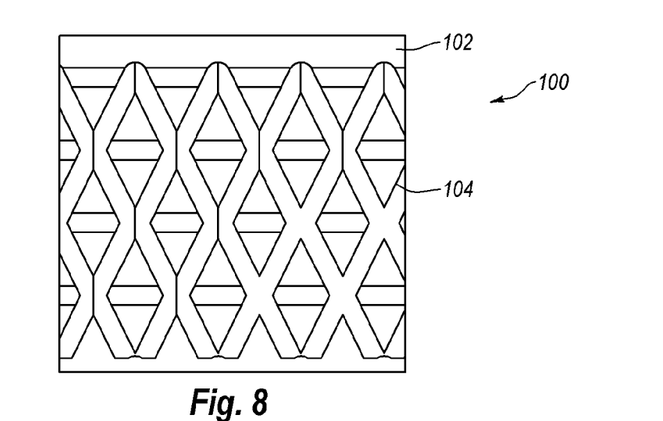
FIG. 8 is a schematic top plan view of another embodiment of a TLC plate intermediate structure similar to FIG. 7, but the catalyst layer exhibits honeycomb-like pattern.
Figure 9:
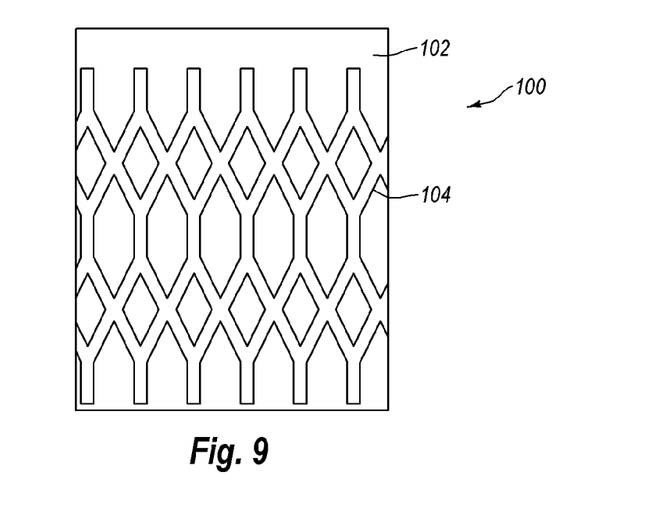
FIG. 9 is a schematic top plan view of another embodiment of a TLC plate intermediate structure similar to FIG. 7, but the catalyst layer exhibits honeycomb-like pattern.
Figure 10:
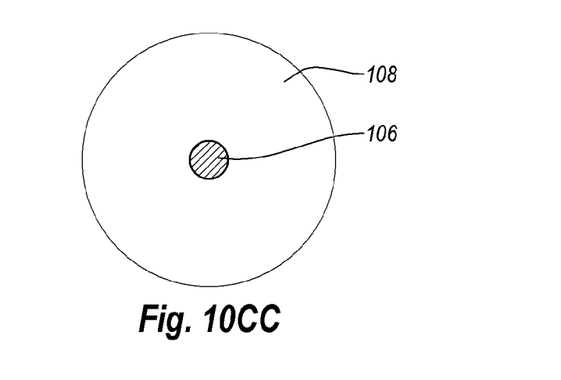
Figure 10A:
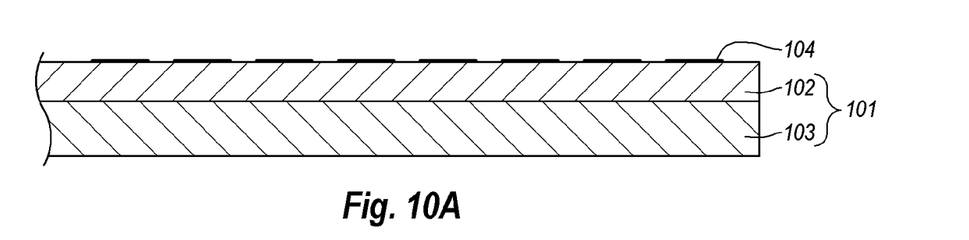
FIG. 10A is a cross-sectional view of the TLC plate intermediate structure of FIG. 1.

A catalyst layer (e.g., iron) may be applied over the backing layer. The catalyst layer may have a thickness between about 0.1 nm and about 10 nm, more particularly between about 0.5 nm and about 8 nm, and even more particularly between about 1 nm and about 5 nm (e.g., about 2 to about 3 nm). The catalyst may be applied so as to form a desired pattern, or may be applied over substantially an entire surface of the backing layer. Various embodiments of patterns for the catalyst layer are shown in FIGS. 1-9. For example, FIGS. 1 and 10A show a TLC plate intermediate structure 100 including a substrate 101 having a backing layer 102 disposed on a base 103 and a catalyst layer 104 formed on backing layer 102 in a zigzag pattern, with the patterned catalyst represented by the dark lines. FIG. 2 illustrates another embodiment of a zigzag pattern for catalyst layer 104, with the patterned catalyst represented by the dark lines. FIGS. 3 and 4 each show a TLC plate intermediate structure 100 including substrate 101 having backing layer 102 disposed on base 103 and catalyst layer 104 formed on backing layer 102 in substantially parallel patterns according to another embodiment, with the patterned catalyst represented by the dark lines. FIGS. 5 and 6 each shows a TLC plate intermediate structure 100 including substrate 101 having backing layer 102 disposed on base 103 and catalyst layer 104 formed on backing layer 102 in various repeating diamond patterns according to various embodiments, with the diamonds representing the catalyst. FIGS. 7-9 each shows a TLC plate intermediate structure 100 including a substrate 101 having backing layer 102 disposed on base 103 and catalyst layer 104 formed on backing layer 102 in different honeycomb-like patterns according to various embodiments.

Catalyst layer 104 may be patterned to exhibit any desired spacing between adjacent portions of the patterned catalyst layer 104. For example, an average bed spacing "S" is shown in FIG. 1. In one embodiment, an average bed spacing between adjacent portions of patterned catalyst layer 104 is between about 1 µm and about 50 µm, more particularly between about 3 µm and about 20 µm, and most particularly between about 5 µm and about 15 µm (e.g., about 10 µm). One of skill in the art will appreciate that catalyst layer 104 may be formed so as to have any desired pattern. In another embodiment, the catalyst layer 104 may be formed so as to cover substantially the entire backing layer 102, lacking any particular distinct pattern. In some embodiments, catalyst layer 104 is spaced inwardly from edges of backing layer 102 in order to substantially prevent growth of CNTs on the edges.

With the catalyst layer 104 formed on the backing layer 102, the TLC plate intermediate structure 100 may be placed onto a suitable support (e.g., a quartz support) within a furnace and heated to a temperature within a range of about 600° C. to about 900° C., more particularly between about 650° C. to about 850° C., and even more particularly to between about 700° C. to about 800° C. (e.g., about 750° C.). A process gas (e.g., $H_2$, ammonia, $N_2$, or combinations thereof) and a carbon-containing gas (e.g., acetylene, ethylene, ethanol, and/or methane) are introduced and flowed over the catalyst layer. A noble gas (e.g., argon) may also be included with the carbon-containing gas stream to control the rate of growth of CNTs on and over the catalyst layer 104. Flow of the process gas and carbon-containing gas may be within a ratio of about 0.5:1 to about 1, more particularly between about 0.55:1 and about 0.85:1, and even more particularly between about 0.6:1 and about 0.8:1.

Once the desired height of CNT growth is achieved, flow of the process gas and carbon-containing gas are turned off, and the furnace chamber may be purged with flow of a noble gas (e.g., argon) as the furnace is partially cooled, for example to a temperature between about 100° C. to about 300° C., more particularly between about 150° C. to about 250° C., and even more particularly to between about 175° C. to about 225° C. (e.g., about 200° C.).

In one embodiment, and in order to achieve a higher aspect ratio of base width to CNT height, a "start/stop" method may be employed. For example, the carbon-containing gas may be turned off during CNT growth, causing the CNTs to grow in a myriad of directions. This type of growth may be desired in some embodiments, as it may lead to more mechanically stable CNTs.

Figure 10B:
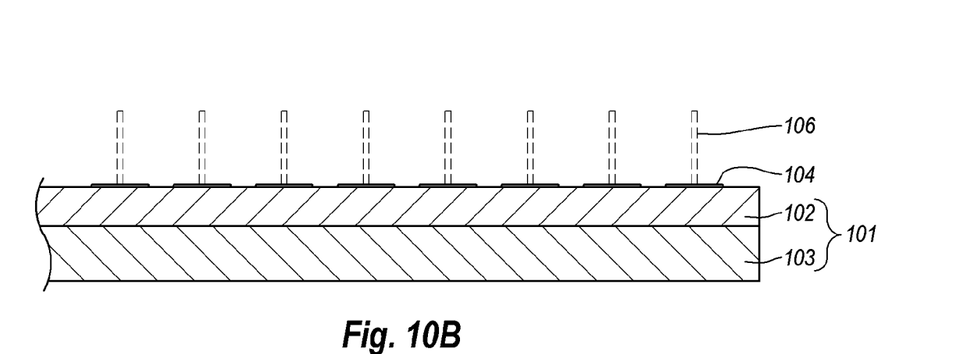
FIG. 10B is a cross-sectional view of the TLC plate intermediate structure of FIG. 10A with CNTs grown on the catalyst layer.

FIG. 10B is a cross-sectional view of an embodiment of a structure similar to that of FIGS. 1 and 10A in which CNTs 106 have been grown on and over catalyst layer 104. CNTs 106 may be grown to extend longitudinally away from the substrate 101. For example, the CNTs may extend substantially perpendicular (i.e., vertical) to catalyst layer 104 and substrate 101. Grown CNTs 106 may be single walled or multi-walled, as desired. Grown CNTs 106 may have an average diameter between about 3 nm and about 20 nm, more particularly between about 5 nm and about 10 nm (e.g., about 8.5 nm) and an average length of about 10 μm to about 2000 μm, about 10 μm to about 1000 μm, about 10 μm to about 500 μm, about 20 μm to about 400 μm, about 20 μm to about 200 μm, about 100 μm to about 300 μm, about 10 μm to about 100 μm, or about 20 μm to about 200 μm. The grown CNTs 106 may exhibit an average aspect ratio (i.e., ratio of average length to average diameter) of at least $10^{-4}$, about $10^{-4}$ to about $10^{-1}$, about $10^{-3}$ to about $10^{-1}$, or about $10^{-2}$ to about $10^{-1}$. The CNTs 106 exhibit a porous structure.

The average length to which CNTs 106 are grown may be chosen based on the particular chromatography application. For example, the average length of the CNTs 106 may be about 10 μm to about 100 μm for ultra-thin layer chromatography ("UTLC"), the average length of the CNTs 106 may be about 100 μm to about 300 μm for high-performance thin layer chromatography ("HPTLC"), and the average length of the CNTs 106 may be about 500 μm to about 2000 μm for preparative liquid chromatography ("PLC").

Additional details regarding growth of CNTs 106 may be found in U.S. patent application Ser. Nos. 12/239,281 and 12/239,339 entitled X-RAY RADIATION WINDOW WITH CARBON NANOTUBE FRAME. Both of the above applications claim priority to U.S. Provisional Patent Application No. 60/995,881. U.S. patent application Ser. Nos. 12/239,281 and 12/239,339 and U.S. Provisional Patent Application No. 60/995,881 is each incorporated herein, in its entirety, by this reference.

Figure 10C:
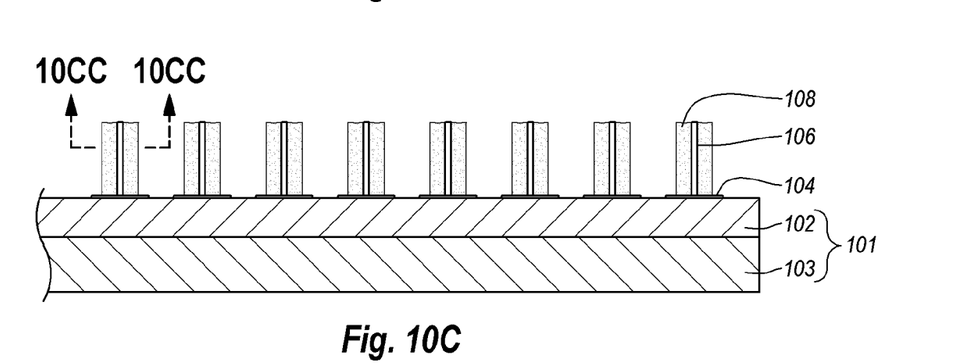
FIG. 10C is a cross-sectional view of the TLC plate intermediate structure of FIG. 10B once the CNTs have been at least partially coated by a coating.

Referring to FIG. 10C, after growth, CNTs 106 may be infiltrated with one or more infiltrants (e.g. a precursor gas) so that a coating 108 deposits on the CNTs 106. The coating 108 comprises a stationary phase and/or a precursor to the stationary phase. Examples of materials for coating 108 include, but are not limited to, elemental silicon, silicon dioxide, silicon nitride, elemental aluminum, aluminum oxide, elemental zirconium, zirconium oxide, elemental titanium, titanium oxide, amorphous carbon, and combinations of the foregoing. Because the choice of coating 108 may change the selectivity of the resulting TLC plate, the coating 108 used for manufacture of any given TLC plate may be selected depending on the intended use of the TLC plate.

In one embodiment, infiltration of the CNTs 106 may be accomplished using chemical vapor deposition (e.g., low pressure chemical vapor deposition) or another suitable deposition process. For example, the TLC plate intermediate structure shown in FIG. 10B may be placed into a furnace and heated to about 500° C. to about 650° C., more particularly between about 540° C. to about 620° C., and even more particularly to between about 560° C. to about 600° C. (e.g., about 580° C.). During infiltration, the infiltration pressure may be maintained at less than about 400 mTorr. For example, the infiltration pressure may be maintained between about 50 mTorr and about 400 mTorr, more particularly between about 100 mTorr to about 300 mTorr, and even more particularly to between about 150 mTorr to about 250 mTorr (e.g., about 200 mTorr). Under such temperature and pressure conditions, the infiltrant flows over CNTs 106 to cause a coating 108 (see FIG. 10C) to form on CNTs 106. The amount of deposition of the coating material achieved may be affected by process time. For example, process time for the infiltration may be between about 0.5 hours and about 10 hours, more particularly between about 1 hours and about 5 hours, and most particularly between about 1 hours and about 4 hours (e.g., about 3 hours).

FIG. 10C is a cross-sectional view of the TLC plate intermediate structure shown in FIG. 10B in which the CNTs 106 have been infiltrated with infiltrant so that a coating material deposits onto the CNTs 106 to form coating 108 that at least partially coats and extends about a periphery of respective CNTs 106. In the case in which the infiltrant is a silicon precursor gas such as silane, coating 108 may be silicon. However, other precursor gases may be used so that coating 108 is formed from aluminum or zirconium. Depending on the infiltrant selected, coating 108 may at least partially or substantially coat the entire array of CNTs 106 only, or it may also coat the intervening portions of backing layer 102 and catalyst layer 104 between the CNTs 106, resulting in a TLC plate that is one coherent mass. Coating 108 on respective CNTs 106 shown in FIG. 10C forms respective high aspect ratio structures exhibiting an elongated annular geometry (e.g., a substantially hollow cylinder). CNTs 106 act as templates around which the coating material deposits. Because CNTs 106 are highly porous, coating 108 is also highly porous. The particular aspect ratio of the elongated annular structures made from coating 108 depends on the height of the template CNTs 106, the deposition time, the process temperature (e.g., temperature of infiltrant and of CNTs 106), or combinations of the foregoing process parameters. FIG. 10CC is a close-up top plan view of a single coated CNT 106 of FIG. 10C. An average aspect ratio (i.e., ratio of average length to average diameter) of the plurality of porous elongated structures defined by coating 108 coating respective CNTs 106 may be at least $10^{-5}$, at least about $10^{-4}$, about $10^{-5}$ to about $10^{-3}$, or about $10^{-4}$ to about $10^{-3}$. The average radial thickness of coating 108 coating the CNTs 106 may be about 10 nm to about 100 nm, more particularly about 20 nm to about 80 nm, and even more particularly about 25 nm to about 40 nm (e.g., about 30 nm). The average length of the porous elongated structures defined by coating 108 may be substantially the same or similar as the template CNTs 106.

As described above, an average bed spacing between adjacent portions of patterned catalyst layer 104 may be between about 1 μm and about 50 μm, more particularly between about 3 μm and about 20 μm, and most particularly between about 5 μm and about 15 μm (e.g., about 10 μm). The growth of CNTs 106 followed by infiltration with infiltrant and/or growth of coating 108 around CNTs 106 results in less spacing between adjacent porous elongated structures defined by coating 108 as they grow laterally outward and towards one another. For example, an average spacing between adjacent porous elongated structures defined by coating 108 may be between about 0.5 μm and about 30 μm, more particularly between about 2 μm and about 10 μm, and most particularly between about 4 μm and about 8 μm. Such spacing results in a bulk structure having very high bulk porosity (i.e., the spacing between adjacent structures act as pores through which the mobile phase and sample carried therewith advance as a result of capillary action. Internal porosity of any individual coating 108 (i.e., as opposed to bulk porosity resulting from spacing between adjacent structures) may also significantly contribute to the overall porosity TLC plate.

In an embodiment, CNTs 106 may be partially or substantially completely removed once the coating 108 has been deposit onto CNTs 106. For example, the TLC plate intermediate structure shown in FIG. 10C may be placed into a furnace and heated (e.g., to about 800° C. to about 900° C., or about 850° C.) in the presence of an oxidizing atmosphere (e.g., an oxygen atmosphere) so as to remove (e.g., burn off) substantially all of CNTs 106, leaving only coating 108 disposed on the backing layer 102 and catalyst layer 104 of TLC plate substrate 101. Such an oxidation step may also serve to convert the coating 108 into the stationary phase by oxidizing the as-deposited coating 108 if it is not already a stationary phase. For example, if the coating 108 is silicon, aluminum, or zirconium, it may be oxidized to silicon oxide, aluminum oxide, or zirconium oxide, respectively. An embodiment of a method for removal of the CNTs 106 may involve oxidizing the coating 108 using an oxygen plasma. Other methods for at least partially removing the CNTs 106 may include dissolution of the CNTs 106, or removal by any method.

Figure 10D:
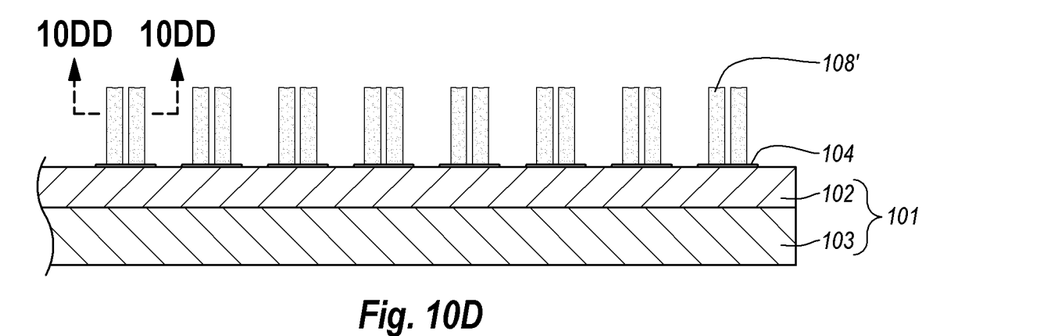
FIG. 10D is a cross-sectional view of the TLC plate intermediate structure of FIG. 10C once the CNTs have been burned off, oxidizing the coating so as to form porous stationary phase structures.

FIG. 10D is a cross-sectional view of the structure shown in FIG. 10C in which the CNTs 106 have been removed and coating 108 has been oxidized to form a plurality of porous elongated stationary phase structures 108'. FIG. 10DD is a top plan view of porous stationary phase structures 108' once CNTs 106 have been burned off. FIG. 10D clearly shows the overall high aspect ratio configuration of the porous stationary phase structures 108'. The dimensions of the plurality of porous elongated stationary phase structures 108' may be substantially the same or similar dimensions as the plurality of porous elongated structures defined by coating 108 prior to oxidation. The oxidation process may occur for at least about 5 hours, more particularly at least about 10 hours, and most particularly for at least about 24 hours. The inventors have found that increased oxidation increases the separation efficiency achieved by the oxidized stationary phase. In some embodiments, only a portion of the coating 108 coating respective CNTs 106 is oxidized. In other embodiments, substantially all of the coating 108 coating respective CNTs 106 is oxidized.

Removal of CNTs 106 before use of the TLC plate may prevent CNTs 106 from interfering (e.g., through a secondary interaction) with separation of a mobile phase during use of the TLC plate. In embodiments in which the coating 108 comprises amorphous carbon, the CNTs 106 may not be removed, as both the coating 108 and CNTs 106 comprise carbon, thereby substantially eliminating the possibility of a secondary interaction as a result of the CNTs 106 being present in the stationary phase formed during infiltration.

In some embodiments, the porous stationary phase structures 108' comprises a material that is white, off white, or generally light in color so that the compounds of the mobile phase separated during use of the TLC plate are visible on the surface of the TLC plate after being developed. Silicon and/or silicon dioxide are examples of materials that provide such a color contrast. In some embodiments, a fluorescent material (e.g., ZnS) may be incorporated in the TLC plate. For example, the fluorescent material may at least partially coat and/or may be incorporated in the porous stationary phase structures 108', may at least partially coat intervening portions of backing layer 102 between the porous stationary phase structures 108', or both.

After oxidation and removal of CNTs 106, in some embodiments, the TLC plate so formed may be placed in a furnace in the presence of HCl so that HCl vapors result in placement of hydroxyl groups onto the surface of porous stationary phase structures 108' to functionalize porous stationary phase structures 108'. Additional chemical functionality and selectivity may be added to the porous stationary phase structures 108' by, for example, silanolization with alkyl moieties through any suitable gas phase chemistry. When the porous stationary phase structures 108' comprise silica (e.g., by oxidizing a silicon coating 108), the silica may be functionalized by bonding $C_8$ chains, $C_{18}$ chains, $NH_2$, or combinations thereof to the silica.

In some embodiments, substrate 101 may be scribed or partially cut before or after growth of CNTs 106 and/or coating CNTs 106. By scribing or cutting substrate 101, smaller TLC plates may be fabricated by breaking a larger TLC plate along a scribe/cut line of substrate 101.

Figure 11A:
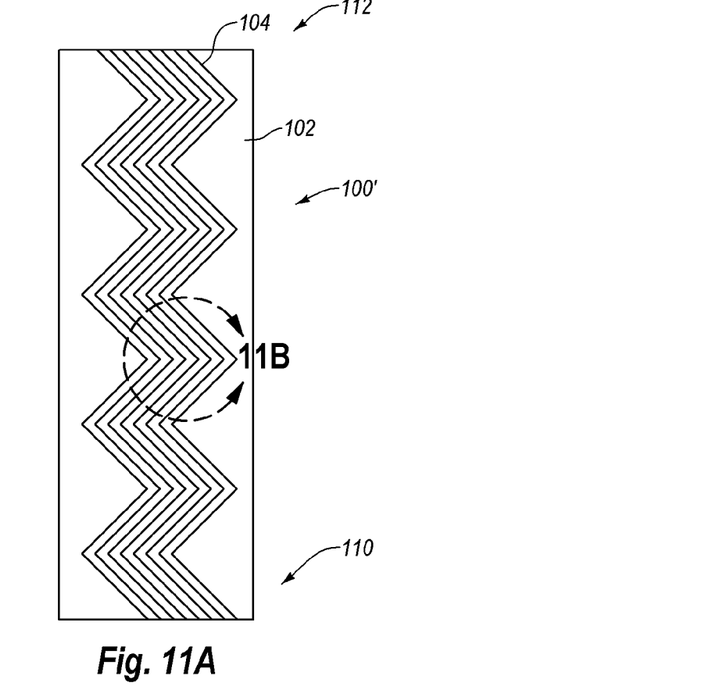
FIG. 11A is a schematic top plan view of a TLC plate manufactured from a TLC plate intermediate structure similar to that of FIG. 1.
Figure 11B:
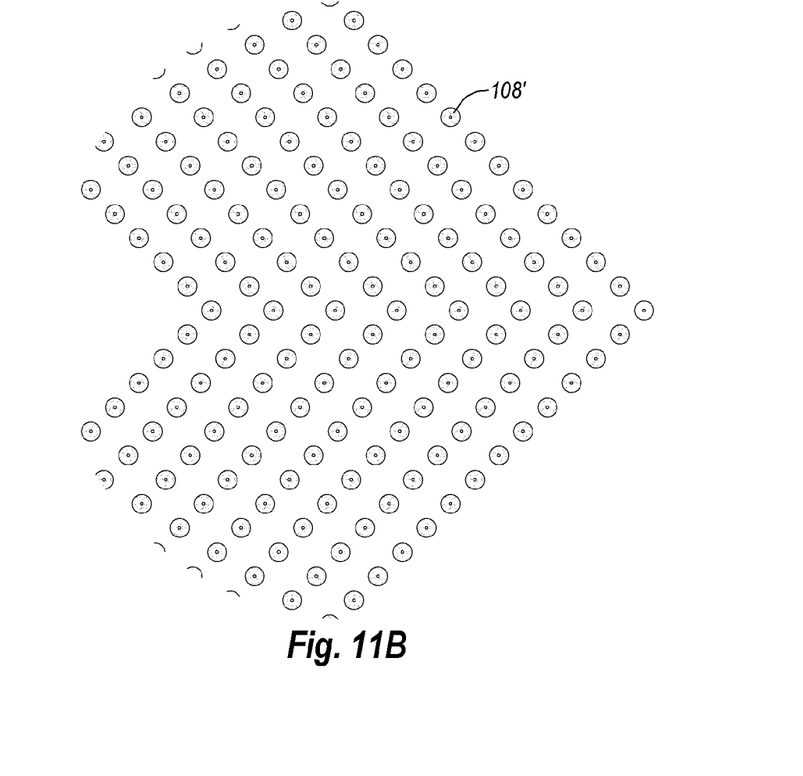
FIG. 11B is a close-up top plan view of the TLC plate intermediate structure of FIG. 11A showing several of the high aspect ratio deposited porous stationary phase structures disposed on the TLC plate substrate.

FIG. 11A is a top plan view of an embodiment of a TLC plate 100'. FIG. 11B is a close up view of a portion of TLC plate 100' includes porous stationary phase structures 108' that are arranged between an end 110 and an end 112 of TLC plate 100'. TLC plates prepared according to the inventive methods disclosed herein provide a stationary phase in which the stationary phase is affixed to the substrate of the TLC plate without the use of any separate binding agent (e.g., typically calcium sulfate). Such binding agents can interfere with the performance of the TLC plate as the result of secondary interactions resulting from the binding agent. The elimination of the need for any binding agent results in a more high efficiency TLC plate while minimizing and/or preventing such secondary interactions.

The spacing of the porous stationary phase structures 108' is illustrated in FIGS. 11A and 11B as being generally uniform. However, in some embodiments, the density of the porous stationary phase structures 108' may be different (e.g., greater or less) in different locations of the TLC plate 100'. For example, the density of the porous stationary phase structures 108' may be different (e.g., greater or less) near end 110 than near end 112. As an alternative to or in addition to the density of the porous stationary phase structures 108' varying with location, the composition of the porous stationary phase structures 108' may vary with location. As a non-limiting example, one portion of the porous stationary phase structures 108' may comprise zirconium oxide and another portion of the porous stationary phase structures 108' may comprise silica.

Furthermore, TLC plates prepared according to the inventive methods disclosed herein provide a stationary phase having a particularly high porosity. The high porosity, as well as the absence of a binder may result in increased efficiency of the TLC plate during use in analyzing a sample within a mobile phase. In one embodiment, the TLC plates formed according to the disclosed methods are used to analyze a sample material. In one embodiment, the sample to be analyzed is applied to the porous stationary phase structures 108' of TLC plate 100' (e.g., near end 110). A mobile phase solvent or solvent mixture is then drawn along TLC plate 100' (e.g., upwardly) by capillary action (e.g., by placing TLC plate 100' in a container including the solvent or solvent mixture). As the solvent or solvent mixture is drawn along the TLC plate 100' via capillary action toward opposite end 112, the sample is dissolved in the mobile phase and separation of components within the sample is achieved because different components of the sample ascend the TLC plate 100' at different rates. The high aspect ratio porous stationary phase structures 108' (e.g., hollow substantially cylindrical structures) as well as the high porosity both within each stationary phase structure 108' as well as the bulk porosity as a result of the spacing between individual high aspect ratio stationary phase structures 108' results in excellent separation efficiency of components within the sample as the sample components are carried through the stationary phase structures 108' by the mobile phase (e.g., a solvent or solvent mixture). The TLC plates 100' may also be used in HPTLC in which one or more of the method of use steps may be automated so as to increase the resolution achieved and to allow more accurate quantization.

III. Working Examples

The following working examples are for illustrative purposes only and are not meant to be limiting with regards to the scope of the specification or the appended claims.

Individual TLC plates were formed by applying a 30 nm alumina layer over a backing layer. A 2-3 nm film of iron catalyst was deposited on the alumina layer and patterned by photolithographic process to form a TLC plate intermediate structure. The TLC plate intermediate structure was placed in a quartz support tube in a furnace and heated to about 750° C. while flowing about 500 standard $cm^3$/min of $H_2$ process gas through the quartz tube. Once the furnace reached about 750° C., a flow of carbon-containing $C_2H_4$ gas was initiated at a flow of about 700 standard $cm^3$/min. After growth of the CNTs were accomplished, the flow of $H_2$ and $H_2H_4$ gases were turned off, and the quartz tube was purged with argon at a flow of about 350 standard $cm^3$/min while the furnace cooled to about 200° C. The grown CNTs had a diameter of about 8.5 nm.

The grown CNTs were coated with silicon using a low pressure chemical vapor deposition process to deposit undoped polycrystalline silicon. The CNTs were placed in a low pressure chemical vapor deposition furnace and heated to about 580° C. at a pressure of about 200 mTorr while flowing about 20 standard $cm^3$/min of $SiH_4$ for approximately 3 hours. The low pressure chemical vapor deposition process coated both the CNTs and the alumina layer. After coating with silicon, the coated TLC plate intermediate structure was placed into a furnace and heated to about 850° C. and held at that temperature while being exposed to the atmosphere, resulting in removal of the CNTs, as well as oxidation of the deposited silicon to silicon dioxide. Different oxidation samples were prepared in which oxidation was conducted for about 5 hours, about 10 hours, and about 24 hours. Testing showed that an increased oxidation time increases the ability of an analyte of the mobile phase to migrate through the silicon/silicon dioxide stationary phase.

Figure 12A:
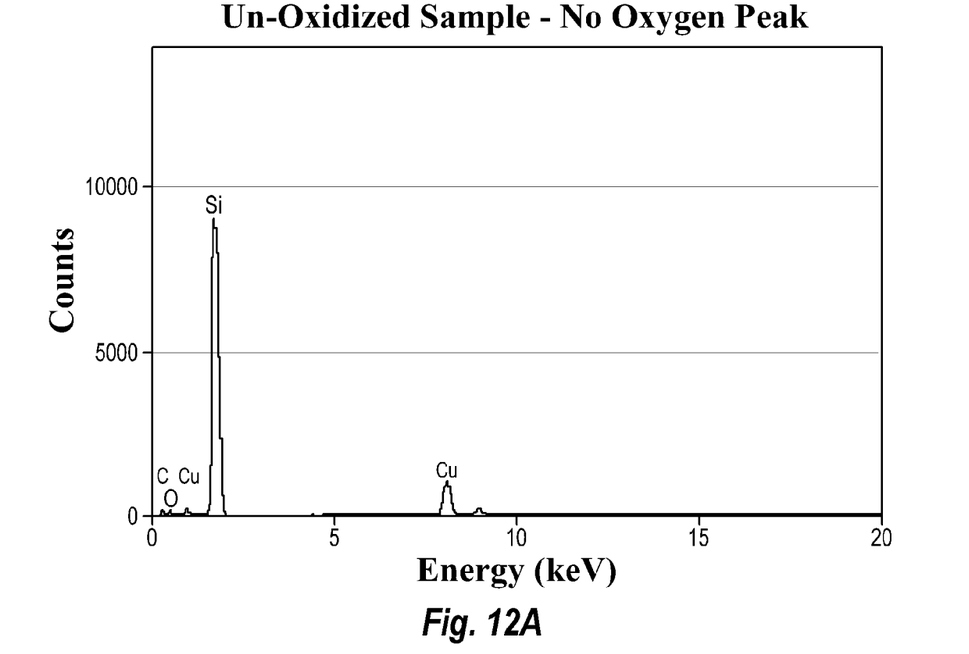
FIGS. 12A and 12B show graphs illustrating energy dispersive x-ray spectroscopy ("EDX") spectra of a TLC plate before and after oxidation according to working examples of the invention.
Figure 12B:
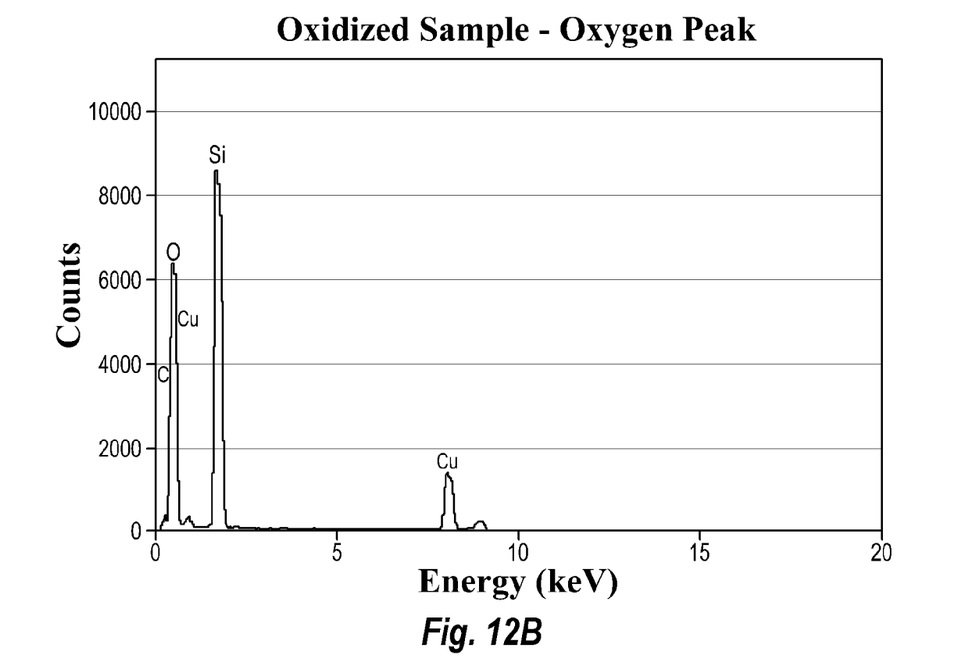

FIGS. 12A and 12B show EDX spectra of the plate before and after oxidation. Before oxidation, carbon is present. After oxidation, minimal carbon remains. Moreover, oxygen is chemically grafted onto the surface of the silicon, forming silicon dioxide.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be opened ended and have the same meaning as the word "comprising" and variants thereof (e.g., "comprise" and "comprises").

What is claimed is:

1. A method for manufacturing a separation plate without the use of a separate binder, the method comprising:
    forming a layer of elongated nanostructures over a substrate;
    at least partially coating the elongated nanostructures with a coating, the coating including at least one of a stationary phase or a precursor of a stationary phase for use in chromatography;
    oxidizing the coating so that a plurality of porous stationary phase structures are formed, the plurality of porous stationary phase structures defines respective porous elongated structures that extend longitudinally away from the substrate; and
    substantially concurrently with the act of oxidizing, removing at least a portion of the elongated nanostructures that have been at least partially coated.

2. The method as recited in claim 1, wherein the coating that at least partially coats the elongated nanostructures defines respective porous elongated annular structures that extend longitudinally away from the substrate.

3. The method as recited in claim 1, wherein forming a layer of elongated nanostructures over a substrate comprises growing the layer of elongated nanostructures on a catalyst layer disposed on a substrate.

4. The method as recited in claim 3, wherein the catalyst layer comprises iron.

5. The method as recited in claim 4, wherein the catalyst layer exhibits a thickness between about 1 nm and about 5 nm.

6. The method as recited in claim 3, wherein the catalyst layer is formed by coating substantially all of a surface of the substrate.

7. The method as recited in claim 3, wherein the catalyst layer is formed on the substrate in a selected pattern.

8. The method as recited in claim 3, wherein the substrate comprises a backing layer on which the catalyst layer is disposed, the backing layer including at least one material selected from the group consisting of silica, silicon, alumina, borosilicate glass, and steel.

9. The method as recited in claim 3, wherein growing the layer of elongated nanostructures on the catalyst layer disposed on a substrate comprises growing a layer of carbon nanotubes.

10. The method as recited in claim 9, wherein the substrate and the catalyst layer are heated to between about 700° C. and about 800° C. during the act of growing the layer of carbon nanotubes.

11. The method as recited in claim 1, wherein at least partially coating the elongated nanostructures with a coating comprises forming the coating to include at least one material selected from the group consisting of silicon, silicon dioxide, silicon nitride, aluminum, aluminum oxide, zirconium, and zirconium oxide.

12. The method as recited in claim 11, wherein forming the coating to include at least one material selected from the group consisting of silicon, silicon dioxide, silicon nitride, and aluminum oxide comprises at least partially infiltrating the elongated nanostructures by low pressure chemical vapor deposition with an infiltrant.

13. The method as recited in claim 12, wherein the low pressure chemical vapor deposition process is carried out at a temperature between about 560° C. and about 600° C. and a pressure between about 100 mTorr and about 300 mTorr.

14. The method as recited in claim 13, further comprising functionalizing the plurality of porous stationary phase structures.

15. The method as recited in claim 1, wherein removing at least a portion of the elongated nanostructures comprises heating the elongated nanostructures in an oxidizing environment so that the elongated nanostructures are substantially removed.

16. A method for manufacturing a separation plate without the use of a separate binder, the method comprising:
   forming a layer of carbon nanotubes over a substrate;
   at least partially coating the carbon nanotubes with a stationary phase having a coating thickness of about 10 nm to about 100 nm;
   removing at least a portion of the carbon nanotubes that have been at least partially coated; and
   bonding functionalizing moieties to the stationary phase for functionalizing the stationary phase.

17. The method as recited in claim 16, wherein removing at least a portion of the carbon nanotubes that have been at least partially coated includes oxidizing the carbon nanotubes.

18. The method as recited in claim 16, wherein the stationary phase comprises silica.

* * * * *